United States Patent [19]
Giese et al.

[11] Patent Number: 5,916,908
[45] Date of Patent: Jun. 29, 1999

[54] PHARMACEUTICAL PYRAZOLE COMPOSITIONS USEFUL AS INHIBITORS OF PROTEIN KINASES

[75] Inventors: Neill A. Giese; Nathalie Lokker, both of San Francisco; Alan M. Laibelman, Menlo Park; Robert M. Scarborough, Belmont, all of Calif.

[73] Assignee: COR Therapeutics, Inc., South San Francisco, Calif.

[21] Appl. No.: 08/556,178

[22] Filed: Nov. 9, 1995

Related U.S. Application Data

[63] Continuation-in-part of application No. 08/337,630, Nov. 10, 1994, abandoned.

[51] Int. Cl.$^6$ .......................... A61K 31/415; C12N 9/99; C12N 9/12
[52] U.S. Cl. .......................... 514/406; 435/184; 435/194
[58] Field of Search ........................... 435/184, 194; 514/406

[56] References Cited

U.S. PATENT DOCUMENTS

| | | | |
|---|---|---|---|
| 4,622,330 | 11/1986 | Bochis et al. | 514/313 |
| 5,196,446 | 3/1993 | Levitzki et al. | 514/415 |
| 5,264,431 | 11/1993 | Wacker et al. | 514/211 |
| 5,382,675 | 1/1995 | Wacker | 549/420 |
| 5,409,930 | 4/1995 | Spada et al. | 514/248 |
| 5,605,820 | 2/1997 | Timberlake et al. | 435/172.2 |

FOREIGN PATENT DOCUMENTS

| | | |
|---|---|---|
| 49100080 | 8/1974 | Japan . |
| 49-100080 | 9/1974 | Japan . |
| 1-258695 | 10/1989 | Japan . |
| WO 94/13643 | 6/1994 | WIPO . |
| WO 94/13644 | 6/1994 | WIPO . |

OTHER PUBLICATIONS

L. Cecchi et al., "Synthesis and Reactivity of 1–Methyl–3–phenyl–4–diazo–5–benzoylamido–pyrazole. A Potential Antitumor Agent", *J. Heterocyclic Chem.*, vol. 21, pp. 957–959 (1984).

L. Cecchi et al., "Carbon–13 NMR Study of 1–Methyl–3–phenyl–4–diazo–5–benzoylamido–pyrazole and Other Model Pyrazole Compounds", *J. Heterocyclic Chem.*, vol. 22, pp. 951–952 (1985).

N. Velasco et al., "Calculations of Molecular Orbitals in Prototypes Derived From 5–Aminopyrazole", *An. R. Acad. Farm.*, vol. 50(4), pp. 617–623 (1984)—Abstract Only.

*Primary Examiner*—Jon P. Weber
*Attorney, Agent, or Firm*—Cooley Godward LLP

[57] ABSTRACT

A method for selectively inhibiting a kinase is disclosed, which comprises contacting a composition containing a kinase with a compound of the formula:

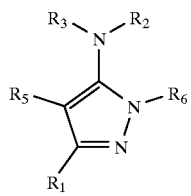

wherein: $R_1$ is lower alkyl, lower hydrocarbyl, aryl lower alkyl, heteroaryl lower alkyl, 5- or 6-membered heterocyclic aromatic, polyaromatic, polyaromatic carbonyl, polyheteroaromatic or polyheteroaromatic carbonyl; $R_2$ is lower alkyl, lower hydrocarbyl, aryl lower alkyl, heteroaryl lower alkyl, 5- or 6-membered heterocyclic aromatic, lower hydrocarboyl, 5- or 6-membered heterocyclic aromatic carbonyl, polyaromatic or polyheteroaromatic; $R_3$ is H or lower alkyl; $R_5$ is H, lower alkyl, lower hydrocarbyl, aryl lower alkyl, heteroaryl lower alkyl, 5- or 6-membered heterocyclic aromatic, halogen, or cyano; and $R_6$ is H or lower hydrocarboyl.

19 Claims, 1 Drawing Sheet

PHARMACEUTICAL PYRAZOLE COMPOSITIONS USEFUL AS INHIBITORS OF PROTEIN KINASES

This application is a continuation-in-part of U.S. application Ser. No. 08/337,630, filed Nov. 10, 1994 now abandoned.

FIELD OF THE INVENTION

This invention relates to pyrazoles and to newly discovered uses of pyrazoles as inhibitors of protein kinases, especially tyrosine kinases, as reagents in the analysis of kinases and their substrates, and as pharmaceutical compositions useful in the inhibition of processes dependent on kinases, such as cell growth.

BACKGROUND

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factor (EGF), platelet derived growth factor (PDGF), fibroblast growth factor (FGF), and p185HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis, and cell differentiation.

Cell replication can be triggered by the exposure of cells to one or more growth factors, examples of which are FGF, EGF, and PDGF. Such growth factors specifically interact with their corresponding receptors, which receptors comprise an extracellular domain, a transmembrane domain and a cytoplasmic domain which possesses the tyrosine kinase enzymatic activity. The initiation of cellular proliferation is believed to occur when a growth factor binds to the extracellular domain of its receptor at the cell surface. This growth factor-receptor binding induces receptor dimerization which results in receptor autophosphorylation, an increase in enzymatic activity of the receptor and substrate phosphorylation. Recently, a common pathway for signaling from the cell surface to the nucleus has been identified and shown to be utilized by the tyrosine kinase growth factor receptors. This pathway involves the growth factor mediated activation of the ras protein which initiates a protein kinase cascade that leads to the phosphorylation of transcriptional factors that regulate the expression of genes involved in cell division.

Receptor autophosphorylation and the phosphorylation of intracellular substrates are biochemical events which are required for growth factor signaling and cell proliferation. This has been demonstrated by eliminating the protein tyrosine kinase activity of a number of receptors including the EGF receptor (EGFR), the FGF receptor (FGFR) and the PDGF receptor (PDGFR) by site-directed mutagenesis which results in the complete loss of the receptors biological activity. Also, protein kinase inhibitors such as Staurosporin, K252a and the tyrphostins which block receptor tyrosine kinase enzymatic activity prevent intracellular signaling and cell proliferation. These studies confirm the essential role of tyrosine phosphorylation in signaling by the growth factor receptors and demonstrate that compounds that inhibit tyrosine kinase activity can be used to regulate cell proliferation.

Many disease states are characterized by uncontrolled cell proliferation. These diseases involve a variety of cell types and include disorders such as cancer, psoriasis, pulmonary fibrosis, glomerulonephritis, atherosclerosis and restenosis following angioplasty. The utility of tyrosine kinase inhibitors for the treatment of such disorders has been demonstrated in a number of in vivo studies. Tyrosine kinase inhibitors with selectivity for the EGFR family have been shown to block tumor formation in animals, thus demonstrating their potential usefulness for directly suppressing tumor cell growth in the treatment of human cancer, especially breast carcinoma. Also, tumor metastasis and its associated angiogenesis has been shown to be inhibited by preventing the activation of the vascular endothelial growth factor receptor tyrosine kinase which indicates a utility for tyrosine kinase inhibitors in blocking separate events that occur during carcinogenesis.

In experimental models of glomerulonephritis, a 20-fold increase in PDGFR expression is associated with mesangial cell proliferation. Neutralization of PDGF which prevents the activation of its tyrosine kinase receptor limits the amount of renal degeneration which normally occurs. These studies demonstrate that a tyrosine kinase inhibitor which blocks PDGFR could have potential for the treatment of human glomerulonephritis.

One major unsolved problem of interventional cardiology is restenosis following coronary angioplasty. Of the nearly 400,000 angioplasties currently performed in the United States each year, 30–40% fail within the first year due to restenosis. The process of restenosis involves the reocclusion of an atherosclerotic artery which in many cases is due to the proliferation of smooth muscle cells which is mediated by growth factors such as PDGF and FGF. In animal models of restenosis, antibodies which block the activation of PDGF or FGF receptor tyrosine kinase activity prevent smooth muscle cell proliferation and the formation of neointima. These studies indicate that tyrosine kinase inhibitors that block PDGF or FGF receptor function could have utility in treating human restenosis.

Currently the chemotherapy of cancer makes use of inhibitors of DNA synthesis (e.g. adriamycin, fluorouracil) and compounds which disrupt the cytoskeleton (vinblastine). These compounds are highly toxic since their inhibitory activity is not limited to cancer cells, with the distinction, however, that tumor cells are more readily attacked by the aforesaid inhibitors because these cells divide more rapidly and their DNA metabolism is consequently more active. A few types of cancers are treated with specific hormone derivatives. These cases, however, are the exception and the chemotherapeutic treatment for the majority of the various types of cancer is non-specific.

In the early 1980's it became apparent that 20 to 30 percent of cancers express characteristic oncogenic products which are growth factor receptors or their mutated homologs, and which exhibit protein tyrosine kinase (PTK) activity. The PTK activity is intrinsic to the receptor or its oncogene homolog and influences the cell proliferation via its PTK domain. Furthermore, each of these receptors (normal or mutated) exhibits a characteristic PTK activity with a distinct substrate specificity. One of these receptors is EGFR and its oncogenic homolog V-ERB-B.

As a result of the above-described developments regarding the PTK activity of growth factor receptors, it has been proposed to treat cancer by means of various chemical substances capable of inhibiting the PTK activity of EGF. See, for example, Japanese patent Nos. 62-39523, 62-39558, 62-42923 and 62-42925. For example, aforementioned Japanese Laid-open Patent No. SHO 62-39558 discloses alpha-cyano-2,5-dihydroxycinnamamide as the active compound in compositions effective as PTK inhibitors.

The use of cinnamyl malononitrile and various benzylidene malononitrile compounds as tumor growth inhibitors is disclosed in Gal et al., Studies on the Biological Action of Malononitriles. I. The Effect of Substituted Malononitriles on the Growth of Transplanted Tumors in Mice, Cancer Research, 12:565-72, 1952.

Yoshida, et al., Japanese Patent Appn. No. 49100080 describes 3-aminopyrazole derivatives that are said to have anti-inflammatory and analgesic effects.

SUMMARY OF THE INVENTION

Accordingly, it is an object of the present invention to provide new and useful formulations of pyrazoles as kinase inhibitors.

It is further an object of the present invention to provide additional uses for old compositions, and to provide new pyrazoles useful as protein kinase inhibitors.

These and other objects of the invention have been accomplished by providing a method for inhibiting a protein kinase, which comprises contacting a composition containing said kinase with a compound of the formula (I) below:

(I)

wherein:
R$_1$ is lower alkyl, lower hydrocarbyl, aryl lower alkyl, heteroaryl lower alkyl, 5- or 6-membered heterocyclic aromatic, polyaromatic, polyaromatic carbonyl, polyheteroaromatic or polyheteroaromatic carbonyl;
R$_2$ is lower alkyl, lower hydrocarbyl, aryl lower alkyl, heteroaryl lower alkyl, 5- or 6-membered heterocyclic aromatic, lower hydrocarboyl, 5- or 6-membered heterocyclic aromatic carbonyl, polyaromatic or polyheteroaromatic;
R$_3$ is H or lower alkyl;
R$_5$ is H, lower alkyl, lower hydrocarbyl, aryl lower alkyl, heteroaryl lower alkyl, 5- or 6-membered heterocyclic aromatic, halogen, or cyano; and
R$_6$ is H or lower hydrocarboyl.

The alkyl, hydrocarbyl, aryl alkyl, heteroaryl alkyl, hydrocarboyl, heterocyclic aromatic, polyaromatic and polyheteroaromatic groups of these compounds can be substituted with various substituents, as discussed in detail below.

The present invention is also directed to pharmaceutical compositions for the control of kinase dependent diseases in mammals which comprise a kinase inhibiting amount of a compound of formula (I) in a pharmaceutically acceptable carrier and to a method of controlling kinase dependent diseases which comprises administering to a mammal suffering from kinase dependent diseases a kinase dependent disease controlling amount of a compound of the formula shown above. Here "mammal" has the usual meaning and includes humans in addition to other mammals. Pharmaceutical uses are intended to include veterinary uses, especially use in domesticated animals such as cattle, sheep, pigs, goats, dogs, cats, rabbits, hamsters, gerbils, rats, and mice.

Other features and advantages will be apparent from the specification and claims.

BRIEF DESCRIPTION OF THE DRAWINGS

The invention will be better understood by reference to the following detailed description in combination with the figures that form part of this specification, wherein.

DESCRIPTION OF SPECIFIC EMBODIMENTS

The present invention is directed to a new use of substituted pyrazoles, some of which are previously known compounds, and some of which are new compounds. These pyrazoles are preferably 3,5-disubstituted pyrazoles or 3,4,5-trisubstituted pyrazoles. One preferred compound useful in the methods of the invention has a phenylcarboxamide substituent at the 3 position of the pyrazole ring and a phenyl substituent at the 5 position. Many compounds of this class are known, but have not previously been known to have activity as kinase inhibitors.

In general, the compounds useful in the methods of this invention have the formula (I):

(I)

wherein:
R$_1$ is lower alkyl, lower hydrocarbyl, aryl lower alkyl, heteroaryl lower alkyl, 5- or 6-membered heterocyclic aromatic, polyaromatic or polyheteroaromatic;
R$_2$ is lower alkyl, lower hydrocarbyl, aryl lower alkyl, heteroaryl lower alkyl, 5- or 6-membered heterocyclic aromatic, lower hydrocarboyl, 5- or 6-membered heterocyclic aromatic carbonyl, polyaromatic, polyaromatic carbonyl, polyheteroaromatic or polyheteroaromatic carbonyl;
R$_3$ is H or lower alkyl;
R$_5$ is H, lower alkyl, lower hydrocarbyl, aryl lower alkyl, heteroaryl lower alkyl, 5- or 6-membered heterocyclic aromatic, halogen, or cyano; and
R$_6$ is H or lower hydrocarboyl.

Included within these definitions are alkyl, hydrocarbyl, aryl alky, heteroaryl alkyl, hydrocarboyl, heterocyclic aromatic, polyaromatic and polyheteroaromatic groups that are independently substituted with (i.e., a hydrogen or hydrogens is replaced by) up to four $R_4$ groups (preferably no more than three, more preferably no more than two, on any one of the three R groups in the formula), where each $R_4$ independently represents halogen, cyano, nitro, lower alkyl (which simply gives another hydrocarbyl group), hydroxyl, alkoxyl, carbonyl, carboxyl, amino, alkylamino, dialkylamino, or hydrocarboylamido.

It has now been discovered that these compounds and pharmaceutical compositions containing them can be used to bind with kinase domains and inhibit kinase activity. Such uses are described below in more detail.

Definition of Terms

As employed above and throughout the disclosure, the following terms, unless otherwise indicated, shall be understood to have the following meanings:

"Alkyl" means a saturated aliphatic hydrocarbon which may be either straight- or branch-chained containing from about 1 to about 6 carbon atoms.

"Lower alkyl" means an alkyl group as above, having 1 to about 4 carbon atoms which may be straight- or branch-chained such as methyl, ethyl, propyl, isopropyl, butyl, isobutyl, sec-butyl or tert-butyl. Halogenated alkyl groups, particularly fluorinated alkyl groups, such as $CF_3$, $CH_2CF_3$, and $CF_2CF_3$, are included within the definition of alkyl groups.

"Aryl lower alkyl" and "heteroaryl lower alkyl" mean a "lower alkyl" as previously described, bound to an aryl or heteroaryl group, respectively. The term "aryl" refers to an unsubstituted or substituted aromatic ring, substituted with one, two, three or four $R_4$ substituents. Preferred aryl groups include phenyl, halophenyl, loweralkylphenyl, naphthyl, biphenyl, phenanthrenyl, naphthacenyl, and aromatic heterocyclics. The term "heteroaryl" as used herein refers to any aryl group, containing from one to four heteroatoms, selected from the group consisting of nitrogen, oxygen and sulfur.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Hydrocarbyl" means an organic radical derived from a hydrocarbon molecule by removal of one of its hydrogen atoms. Hydrocarbyl groups include both aliphatic and aromatic hydrocarbons. Aliphatic hydrocarbons can be saturated or unsaturated, branched or straight chain. Phenyl, a carbocyclic aromatic, is the preferred aromatic hydrocarbyl group. "Lower hydrocarbyl" refers to 6 or fewer aliphatic carbon atoms or one phenyl ring.

"Hydrocarboyl" means an organic radical derived from an organic acid, i.e., a carboxylic acid or sulfonic acid, by the removal of its acid hydroxyl group. Preferred hydrocarboyl groups are lower alkyl carboxylic acid groups such as acetyl and propionyl. Benzoyl is also preferred. "Lower hydrocarboyl" refers to 6 or fewer aliphatic carbon atoms or one phenyl ring, not counting the carbonyl carbon through which bonding of the radical to the remainder of the molecule occurs. A "φ" symbol is used to represent a phenyl ring in some formulations in this specification. Compounds formed from sulfonic acids are less preferred, but are included within the meaning of hydrocarboyl, in which case all parts of the radical are carbon or hydrogen other than the sulfonyl group, unless the compound is a substituted hydrocarboyl, as elsewhere defined. Examples include a benzenesulfonyl group.

"Substituted" hydrocarbyl or hydrocarboyl means a hydrocarbyl or hydrocarboyl in which a hydrogen atom or group of hydrogen atoms has been replaced by a substituent such that the resulting compound is stable at a concentration of 0.01 M in water (containing up to 10% ethanol for increased solubility, if necessary) for 1 hour (typically measured at 37° C., pH 7.4). Preferred substituents are halogen, lower alkyl (which simply gives another hydrocarbyl group), hydroxyl, alkoxyl, carbonyl, amino, alkylamino, dialkylamino, or hydrocarboylamido. Additional substituents found more preferably in aromatic hydrocarbyl and hydrocarboyl groups than in aliphatic groups include nitro.

"Halo" means a halogen atom. Preferred halogens include chlorine, bromine and fluorine.

"Heterocyclic aromatic ring" refers to a 5- or 6-membered ring containing carbon atoms and one or more N, O, or S atoms and a 6-electron delocalized conjugated pi bonding system. Such a heterocyclic aromatic ring can replace a phenyl ring in any of the structures described herein. Preferred heterocyclic aromatic rings are furan, thiophene, pyrrole, pyrazole, triazole, imidazole, oxazole, isoxazole, thiazole, isothiazole, pyridine, pyrimidine, pyridazine, pyrazine, and triazine; especially preferred groups are furan, thiophene, pyrrole, thiazole, and pyridine. "Heterocyclic aromatic carbonyl" refers to a heterocyclic aromatic ring attached to a carbonyl, The attachment preferably occurs through a carbon of the aromatic ring such as with 2-furylcarbonyl and 2-thiophenylcarbonyl.

"Polyaromatic" and "polyheteroaromatic" refers to multiple ring systems, preferably those systems containing two rings. The terms are intended to cover both fused ring rings radicals such as naphthyl and quinolyl, and non-fused ring radicals such as biphenyl. "Polyaromatic carbonyl" and "polyheteroaromatic carbonyl" refers to a "polyaromatic" and "polyheteroaromatic" group attached to a carbonyl.

Structure of Sreferred Compounds of Formula (I)

One preferred group of compounds of formula (I) have the following substituents: $R_1$ is lower alkyl, lower hydrocarbyl, or 5- or 6-membered heterocyclic aromatic; $R_2$ is lower alkyl, lower hydrocarbyl, 5- or 6-membered heterocyclic aromatic, lower hydrocarboyl, or 5- or 6-membered heterocyclic aromatic carbonyl; $R_3$ is H or lower alkyl; $R_5$ is H, lower alkyl, halogen, or cyano; and $R_6$ is H or lower hydrocarboyl.

Another preferred group of compounds of formula (I) have the following substituents: $R_1$ is lower hydrocarbyl or 5- or 6-membered heterocyclic aromatic; $R_2$ is lower hydrocarboyl or 5- or 6-membered heterocyclic aromatic carbonyl; $R_3$ is H or lower alkyl; $R_5$ is H; and $R_6$ is H or lower alkylcarbonyl.

Preferred compounds include those where $R_1$ is a lower hydrocarbyl or a 5- or 6-membered heterocyclic aromatic, and is optionally substituted with up to four $R_4$ groups. Even more preferred compounds include those in which $R_1$ is a carbocyclic aromatic such as phenyl or substituted phenyl or a 5-membered heterocyclic aromatic such as thienyl. The most preferred $R_1$ group is phenyl or substituted phenyl.

Preferred compounds include those where $R_2$ is a lower hydrocarboyl or a 5- or 6-membered heterocyclic aromatic carbonyl, and is optionally substituted with up to four $R_4$ groups. Even more preferred compounds include those in which $R_2$ is a lower hydrocarboyl such as a carbocyclic aromatic carbonyl, preferably a phenylcarbonyl or a substituted phenylcarbonyl. Preferred substituents include nitro and amino groups. Also preferred are compounds where $R_2$ is a 6-membered heterocyclic aromatic carbonyl such as nicotinoyl or isonicotinoyl. Most preferred compounds are those where $R_2$ is phenylcarbonyl (i.e., benzoyl) or substituted phenylcarbonyl. Particularly preferred $R_2$ substituents are those containing a phenylcarbonyl or a phenylcarbonyl substituted with an electron-donating or electron neutral substituent (relative to H on the phenyl group), especially alkyl or alkoxy subsituents.

Preferred compounds include those where $R_3$ is H.

Preferred compounds include those where $R_5$ is H, lower alkyl, halogen, or cyano, subject to the substitution limitations set out above. Even more preferred compounds include those where $R_5$ is H Preferred compounds include those where $R_6$ is H.

Exemplary structures of compounds of formula (I) are set out in the table below. Compound 1, a preferred compound where $R_1$ is phenyl, $R_2$ is benzoyl, and $R_3$, $R_5$ and $R_6$ are H, was used in the experimental work described in detail in the Examples section of this specification.

TABLE 1A

| Cmpd | $R_1$ | $R_2$ | $R_3$ | $R_5$ | $R_6$ |
|---|---|---|---|---|---|
| 1 | φ | φCO | H | H | H |
| 2 | φ | 4-ClφCO | H | H | H |
| 3 | φ | 2-FφCO | H | H | H |
| 4 | φ | 2-ClφCO | H | H | H |
| 5 | iPr | φCO | H | H | H |
| 6 | nPn | 4-Clφ | H | H | H |
| 7 | φ | nPr | H | Me | H |
| 8 | HCO(CH$_2$)$_4$ | 4-NH$_2$φCO | H | Me | H |
| 9 | φ | φ | H | Me | H |
| 10 | φ | 2-thiophenylCO | H | Me | H |
| 11 | cyclohexyl | 4-MeφCO | H | Cl | H |
| 12 | 2,4-diMeφ | HCO | H | Cl | H |
| 13 | φ | φCO | Me | F | H |
| 14 | 4-CF$_3$φ | 2,4-diMeφCO | Me | F | H |
| 15 | 3,5-diNO$_2$φ | nBuCO | Et | F | H |
| 16 | 2-furyl | φSO$_2$ | Me | CN | H |
| 17 | iBu | φCO | iPr | CN | H |
| 18 | φ | φCO | 4-hydroxybutyl | CN | H |
| 19 | 2-(5-methylfuryl) | φCO | Me | H | H |
| 20 | φ | φSO$_2$ | H | H | H |
| 21 | nPn | 2,4-diFφSO$_2$ | H | Me | H |
| 22 | 2,4,6-triClφ | φCO | H | CN | H |
| 23 | φ | 4-(φCONH)φCO | H | H | H |
| 24 | HOCO(CH$_2$)$_5$ | 1-[5-(dimethylamino)pentyl]CO | H | H | H |
| 25 | 4-Methylcyclohexyl | 4-(2-methylpyridyl)CO | Me | Cl | H |
| 26 | 2,4-diMeφ | cyclopentylCO | Et | F | H |
| 27 | φ | 4-tBuCO | Et | Et | H |

The following abbreviations are used in Table 1A: Me—methyl; Et—ethyl; nPr—n-propyl; iPr—iso-propyl; nBu—n-butyl; tBu—tert-butyl; nPn—neopentyl (2,2-dimthylpropyl); iBu—iso-butyl; MeCO—acetyl (remaining acyl derivatives named in same manner); φ—phenyl.

The following table lists compounds of the invention that were synthesized in a manner similar to that described in Example 3. The $R_1$–$R_6$ substituents in these compounds are illustrative of substituents that are suitable for use in the present invention and are not intended to be limiting.

Evaluation of their activities was done in a manner similar to that set forth in Example 1. These compounds all inhibited protein kinase activity of the αPDGFR and βPDGFR. The aromatic and heteroaromatic acyl amino pyrazoles, both substituted and unsubstituted, where $R_3$, $R_5$ and $R_6$ are H exhibited the best activities: compounds 37–42, 45 and 46.

TABLE 1B

| Cmpd | $R_1$ | $R_2$ | $R_3$ | $R_5$ | $R_6$ |
|---|---|---|---|---|---|
| 28 | φ | MeCO | H | H | MeCO |
| 29 | φ | MeCO | H | H | H |
| 30 | 4-tBuφ | 4-ClφCO | H | H | H |
| 31 | φ | φCO | H | H | φCO |
| 32 | φ | i-PrCO | H | H | i-PrCO |
| 33 | φ | C$_6$H$_{11}$CO | H | H | C$_6$H$_{11}$CO |
| 34 | φ | i-PrCO | H | H | H |
| 35 | φ | 4-MeφCO | H | H | 4-MeφCO |
| 36 | φ | 4-NO$_2$φCO | H | H | 4-NO$_2$φCO |
| 37 | φ | 4-MeOφCO | H | H | H |
| 38 | φ | 4-MeφCO | H | H | H |
| 39 | φ | 4-NO$_2$φCO | H | H | H |
| 40 | φ | nicotinoyl | H | H | H |
| 41 | φ | 4-NH$_2$φCO | H | H | H |
| 42 | φ | isonicotinoyl | H | H | H |
| 43 | 2-thienyl | φCO | H | H | φCO |
| 44 | 4-Clφ | φCO | H | H | φCO |
| 45 | 4-Clφ | φCO | H | H | H |
| 46 | 2-thienyl | φCO | H | H | H |
| 47 | φ | φCH$_2$ | H | H | H |

The following abbreviations are used in Table 1B: Me—methyl; iPr—iso-propyl; MeCO—acetyl (remaining acyl derivatives named in same manner); tBu—tert-butyl and φ—phenyl.

Preparation and Production of Compounds

Many compounds of the aminopyrazole class useful in the present invention are well known, with synthesis of various compounds being described in the scientific literature for over 30 years. There is some potential confusion on the issue of nomenclature in the literature, which should not cause problems to anyone of skill in the art. This arises because of the symmetrical nature of the pyrazole ring, since either of the two nitrogens can be considered to be the starting point for numbering atoms of the ring. In the formulas above and throughout this application, compounds are consistently named so that the amino substituent appears on the carbon designated "3" in the numbering of the pyrazole ring. However, it would have been equally satisfactory to number the ring in the opposite direction so that the amino substituent appears on carbon 5 and the other substituent appears on carbon 3. Thus, some of the scientific literature refers to 3-aminopyrazoles and some to 5-aminopyrazoles, while meaning the same compound or compounds. The use of nomenclature in a single publication is consistent, however, and there is no confusion overall in the literature once this quirk of nomenclature is understood.

The 3-aminopyrazoles used in the methods of the invention can be prepared and modified by known techniques, as many of these compounds are well known for other uses. 3-Aminopyrazole itself is commercially available, for example, from Aldrich Chemical Company, Inc., Milwaukee, Wis., Missouri, USA (catalogue No. 16,064-4). Pyrazoles can be readily synthesized by the reaction of diazomethane with acetylene. This synthetic pathway to pyrazoles is nearly 100 years old and is well established. See, for example, von Pechmann, *Ber. Deut. Chem. Ges.*, 31:2950 (1898), and Hueckel et al., *Z. Phys. Chem., A*, 186:159 (1940). Various substitution patterns in the resulting pyrazole can be readily prepared by selecting starting alkynes and diazo compounds with the desired substitution pattern.

Other synthetic routes exist for producing 3-aminopyrazoles. For example, a general synthesis of substituted 3-aminopyrazoles is given is U.S. Pat. No. 4,622,330, in which an alkylhydrazine of formula $R_1$—NHNH$_2$ undergoes a condensation reaction with a compound of the formula $AlkOCR_4=C(CN)_2$ to give a product 1-$R_1$-3-$R_4$-4-CN-5-aminopyrazole. This reaction can readily be adapted to produce compounds of the invention by substituting hydrazine for the alkylhydrazine and (if necessary) either removing the cyano group from the product pyrazole, converting it to an alkyl group, or selecting a starting material with only one cyano group. For examples of the synthesis of the compound 3-benzoylamido-5-phenylpyrazole, which is compound 1 in Table 1A, see Huenig, *Chem. Ber.*, 95:937–943 (1962), and Checchi et al., *Gazz. Chim. Ital.*, 85:1558–1568 (1955), both of which are herein incorporated by reference.

Several compounds of particular interest are available commercially from Maybridge Chemical Co. Ltd., Trevillett, Tintagel, Cornwall PL34OHW, United Kingdom, especially 3-[2'-fluorobenzoylamino]-5-phenylpyrazole, 3-[2'-chlorobenzoylamino]-5-phenylpyrazole, 3-benzoylamino-5-phenylpyrazole, and 3-[4'-chlorobenzoylamino]-5-phenylpyrazole. It should be noted here that the names given in the previous sentence are not strictly according to IUPAC nomenclature rules, but are named to retain the nomenclature of the compounds as pyrazoles for consistency in this specification. An alternative name for 3-benzoylamino-5-phenylpyrazole (compound 1) is N-(5-phenyl-1(2)H-pyrazol-3-yl)-benzamide. The latter is the name used in Beilstein (Beilstein Reg. No. 22573; CAS Reg. No. 97620-17-2).

Various substituents on the 3-amino group or on the pyrazole ring can be present in the starting compound or added after formation of the condensation product by methods known in the art for substitution or conversion of one group to another. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. Primary alcohols can be oxidized by oxidizing agents known in the art to form carboxylic acids or aldehydes and secondary alcohols can be oxidized to form ketones. Thus, substitution or alteration reactions can be employed to provide a variety of substituents throughout the molecule of the starting material, intermediates or the final product. Of particular importance is the synthetic route available by hydrolysis of existing carboxamide groups and replacement with another through a simple amidation reaction.

Other examples of scientific publications that give details of synthetic techniques for preparing compounds of the invention, as well as discussions of previously known utilities, include the following, all of which are herein incorporated by reference: Sanz et al., *J. Chem. Soc. Perkin Trans. I*, 1990, pp.809–810; Hammouda et al., *J. Heterocycl. Chem.*, 21:945–947 (1984); and Sawali et al., *J. Heterocycl. Chem.*, 17:877–880 (1980).

Use as Inhibitors of Kinases

The compounds of this invention are all readily adapted to therapeutic use as kinase inhibitors for the control of kinase dependent diseases in mammals, especially those related to tyrosine kinase. Particularly suited are those compounds with an $IC_{50}$ value within the range of 10 nM-1 µM. The ability of a pyrazole acid derivative to specifically inhibit one of the three types of protein kinases in preference to other classes (the three known classes are discussed below) is one of the factors that determines the manner in which a specific compound will be used. Tyrosine kinase dependent diseases include hyperproliferative disorders which are initiated/maintained by aberrant tyrosine kinase enzyme activity. Examples include cancer, atherosclerosis, and anti-angiogenesis (e.g., tumor growth, diabetic retinopathy). Although there is less information available on the relationship of other classes of kinases to specific diseases, it is understood in the art that therapeutically useful PTK inhibiting compounds preferably should be selective, and the same is true for the other classes of kinases. The PTK inhibitors quercetin, genistein, and staurosporin inhibit many other protein kinases in addition to tyrosine kinases and as a result of their lack of specificity are highly cytotoxic. Therefore, routine assays which measure cytotoxicity can be used to identify PTK inhibitors (or inhibitors of other classes of kinases) which are likely to produce undesirable side effects due to a lack of selectivity.

Three general classes of protein kinases have been identified based upon the amino acid(s) that serves as their substrate: kinases that phosphorylate tyrosine, kinases that phosphorylate tyrosine and threonine and kinases that phosphorylate serine and threonine. As a more detailed test of selectivity, compounds should be tested for their ability to inhibit the enzymatic activity of a range of these protein kinases. Tyrosine specific protein kinases are described in the Background section. Examples of kinases that phosphorylate serine and threonine (the most common class) include RAF, protein kinase A, protein kinase C, and transforming growth factor beta receptor. The kinase MEK is an example of kinases that phosphorylate tyrosine and threonine.

In the following discussion of uses of kinase inhibitors, the discussion focuses on tyrosine kinases, since these are the kinases that have been most readily accessible to pharmaceutical control. It should be understood, however, that any discussion here of use of a compound as a tyrosine kinase inhibitor is equally applicable to use of a compound that is specific for one of the other kinase classes, once the specificity of action is known. Whether a pyrazole compound is specific for a particular class of kinase is readily determined by use of the kinase activity assays set out in the examples (or an otherwise identical assay that substitutes a different kinase for the kinase discussed in the example). In order to avoid undue repetition, the following discussion discusses tyrosine kinases as examples of what can be done with other classes of kinases. Thus a reference to "tyrosine kinase" or "PTK" for a particular use or in a particular situation should be taken as an example of a use of a compound specific for any of the kinase classes, unless otherwise specified or clear from the context.

In order for compounds that inhibit PTK or one of the other kinase classes to be therapeutically useful they should be active on intact cells. It is known that PTK inhibitors that are identified on the basis of their ability to inhibit isolated enzyme preparations are often weak or ineffective at inhibiting native PTKs. This lack of activity is due either to the inability of the PTK inhibitors to get across the cell membrane to reach their site of action or they are unable to inhibit PTKs in cells where adenosine triphosphate (ATP) concentrations are high and other factors may be involved. Several methods are readily available for determining the activity of PTK inhibitors against growth factor receptor tyrosine kinases on intact cells. Growth factor treatment of cells results in the rapid autophosphorylation of the corresponding receptor as well as phosphorylation of the receptor's substrates and these events can be measured using antiphosphotyrosine antibodies. Also, additional intracellular signaling events can be measured including calcium flux, inositol phosphate metabolism, and cellular DNA synthesis. Finally, a therapeutically useful PTK inhibitor must be able to block cellular proliferation which is the unwanted outcome of growth factor action and is easy to monitor.

It is theorized that solubility of the compounds of the present invention both in water and in mildly hydrophobic solvents will enhance the probability that they traverse the cell membrane. Various insoluble compounds, however, have exhibited significant kinase inhibition in in vitro testing.

Compounds of this invention may be useful in the form of a free acid or base (if a carboxyl, phenolic hydroxyl, or amino group is present), in the form of a salt, or as a hydrate. All forms are within the scope of the invention. Basic salts may be formed and are simply a more convenient form for use; in practice, use of the salt form inherently amounts to use of the acid form. The acids or bases which can be used to prepare the salts include preferably those which produce, when combined with the free acid or base, pharmaceutically acceptable salts, that is, salts whose cations or anions are non-toxic to the animal organism in pharmaceutical doses of the salts, so that the beneficial properties inherent in the free acid or base are not vitiated by side effects ascribable to the cations. Although pharmaceutically acceptable salts of an acid or base compound are preferred, all salts are useful as sources of the free acid form even if the particular salt per se is desired only as an intermediate product as, for example, when the salt is formed only for purposes of purification and identification, or when it is used as an intermediate in preparing a pharmaceutically acceptable salt by ion exchange procedures.

Compounds within the scope of this invention that have activity as specific inhibitors as protein tyrosine kinase inhibitors possess therapeutic value as cellular antiproliferative agents for the treatment of certain conditions including, for example, psoriasis and restenosis. It is expected that the invention will be particularly applicable to the treatment of atherosclerosis. With regard to the treatment of some conditions, for example, atherosclerosis, certain people may be identified as being at high risk, for example, due to genetic, environmental or historical factors. Compounds within the scope of the present invention can be used in preventing or delaying the occurrence or reoccurrence of such conditions or otherwise treating the condition.

Compounds of the present invention can be administered to a mammalian host in a variety of forms i.e., they may be combined with various pharmaceutically acceptable inert carriers in the form of tablets, capsules, lozenges, troches, hard candies, powders, sprays, elixirs, syrups, injectable or eye drop solutions, and the like depending on the chosen route of administration, e.g., orally or parenterally. Parenteral administration in this respect includes administration by the following routes: intravenous, intramuscular, subcutaneous, intraocular, intrasynovial, transepithelial (including transdermal, ophthalmic, sublingual and buccal), topical (including ophthalmic, dermal, ocular, rectal, nasal inhalation via insulation and aerosol), and rectal systemic.

Accordingly, another aspect of the present invention is a pharmaceutical composition for the control of kinase dependent diseases in mammals which contains a kinase inhibiting amount of a compound of formula (I) in a pharmaceutically acceptable carrier. As noted above, kinase dependent diseases may be controlled by inhibiting kinase activity. Although many compounds of the aminopyrazole class useful in the present invention were well known, none are known to inhibit kinase activity and few have any known therapeutic utility. A preferred pharmaceutical composition contains a compound of formula (I) with the proviso that when $R_1$ is phenyl or phenyl substituted with lower alkyl, lower alkoxy or halogen; $R_3$ and $R_6$ are H; and $R_5$ is lower alkyl, aryl or aryl substituted with lower alkyl, lower alkoxy or halogen, then $R_2$ can not be lower alkyl.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: a binder such as polyvinyl-pyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitable buffered, if necessary, and the liquid diluent first rendered isotonic with sufficient saline or glucose. Solutions of the active compound as a free base or a pharmacologically acceptable salt can be prepared in water suitably mixed with a surfactant such as hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for drop-wise administration to the eye.

The therapeutic compounds of this invention may be administered to a mammal alone or in combination with pharmaceutically acceptable carriers. As noted above, the relative proportions of active ingredient and carrier are determined by the solubility and chemical nature of the compound, chosen route of administration, and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g and higher although it may be administered in several different dosage units from once to several times a day. Oral administration requires higher dosages.

The compounds are administered either orally or parenterally, or topically as eye drops, in dosages ranging from about 0.1 to 10 mg/kg of body weight per day in single or divided doses. Of course, in particular situations, at the discretion of the attending physician, doses outside of this range will be used.

In a pharmaceutical composition comprising a compound of formula (I) or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

The compounds of the present invention are also useful for detecting the presence of tyrosine kinase or a tyrosine kinase substrate in a body fluid such as blood or a blood fraction. The tyrosine kinase activity in a composition is measured in the absence of a compound of the invention and compared to the activity measured in the presence of such compound. The difference in these measured kinase activities is then related to the concentration of tyrosine kinase or tyrosine kinase substrate in the composition.

The invention now being generally described, the same will be better understood by reference to the following detailed examples, which are provided for the purpose of illustration only and are not to be considered limiting of the invention unless otherwise specified.

EXAMPLE 1

Inhibition of Protein Kinase Enzymatic Activity by Pyrazole Compounds

Pyrazole compounds used in this and the following examples were obtained from Maybridge Chemical Co. Ltd., Trevillett, Tintagel, Cornwall PL34OHW, United Kingdom.

The stimulation of cell proliferation by growth factors such as PDGF, FGF and EGF is dependent upon their induction of autophosphorylation of each of their respective receptor's tyrosine kinases. Therefore, the ability of a PTK inhibitor to block cellular proliferation induced by these growth factors is directly correlated with its ability to block receptor autophosphorylation. To measure alpha PDGFR autophosphorylation a previously described mouse hematopoietic cell line, 32D-αR, which had been engineered to overexpresses the human alpha PDGFR was used. These cells were grown in suspension to $10^6$ cells/ml in RPMI (Gibco BRL) media containing 10% fetal bovine serum and 5% WEHI conditioned media (tissue culture media conditioned by WEHI cells available from ATCC) as previously described. The cells were pelleted by low speed centrifugation and resuspended in serum-free RPMI prior to distribution at 500,000 cells/well in 96 well conical bottom microtiter plates (Falcon). Compounds (0.01–30 μM) were added to the wells at room temperature 15 minutes prior to the addition of PDGF AA (15 ng/ml) and the incubation was continued on ice for 90 minutes in a final incubation volume of 100 μl. The cells were then pelleted at 2000 rpm for 10 minutes at 4° C. and 50 μl of freshly prepared lysis buffer (20 mM Tris at pH 7.3, 150 mM NaCl, 1% Triton X-100, 1 mM phenylmethyl-sulfonyl fluoride (PMSF), 1 mM sodium orthovanadate, 10 mg/ml aprotinin and 10 mg/ml leupeptin) was added directly to each well, incubation was continued for 10 minutes on ice and cell lysis was facilitated by vigorous agitation on a plate shaker. The cell lysates were cleared by centrifugation at 2,000 rpm for 10 minutes prior to analysis.

For the analysis of beta PDGFR autophosphorylation, the Chinese hamster ovary (CHO) cell line, HR5-βR, was used which had been engineered to stably overexpress the human beta PDGFR as previously described. These cells were seeded at 10,000 cells/well in microtiter plates (Falcon 96 well plates) and incubated at 37° C. in RPMI with 10% fetal bovine serum for 3 days at which time confluency was reached. The media was removed from the wells and replaced with 100 μl of serum free RPMI and incubation was continued at 37° C. for 18 hours. Compounds (0.01–30 μM) were added to the wells 15 minutes prior to the addition of PDGF BB (100 ng/ml) and the incubation was continued at 37° C. for 10 minutes. The media was drained and 50 μl of freshly prepared lysis buffer was added to each well and the plate was shaken vigorously to prepare the cell lysate. The lysates were then cleared by centrifugation at 2600 rpm for 10 minutes prior to their analysis.

In a separate microtiter plate, monoclonal antibodies (prepared at COR Therapeutics, Inc.) directed against the extracellular domain of the alpha PDGFR (MAb αR10) or the beta PDGFR (MAb 1B5B11) were immobilized by incubating 0.5 μg of antibody per well at 4° C. for 18 hours in 23 mM Tris at pH 8.0, 68 mM NaCl, 14 mM ammonium bicarbonate and 0.01% sodium azide. Unbound antibody was removed and the wells were blocked with 25 mM N-(2-hydroxyethyl)piperazine-N'-(2-ethanesulfonic acid) (HEPES) pH 7.6, 100 mM NaCl, and 0.2% Tween 20 just prior to the addition of cell lysate that had been diluted 1:2 in binding buffer (blocking buffer with 0.3% gelatin). 32D-αR or HR5-βR cell lysate was incubated with immobilized MAb αR10 or MAb 1B5B11, respectively, for 2 hours at room temperature and wells were washed 3 times with 200 μl of wash buffer (phosphate buffered saline "PBS", 0.01% Tween 20). To detect the level of PDGFR phosphorylation, a rabbit anti-phosphotyrosine antibody (Upstate Biotechnology, Inc., "UBI") was added at 1.25 μg/ml and incubated for 1 hour at 37° C. After removal of unbound anti-phosphotyrosine antibody the plates were incubated with goat horseradish conjugated anti-rabbit IgG (Boehringer Mannheim) at 1:1000 dilution prior to the addition of peroxidase substrate (ABTS™). Product formation was monitored at 650 nm using a microtiter plate reader (Molecular Devices).

EGFR autophosphorylation was measured in MDA MB 468 cells (ATCC# HTB 132), a human mammary tumor cell line that overexpresses the EGFR. These cells were grown to confluency in 6-well plates and incubated in serum-free Dulbecco's Modified Eagle Medium (DMEM) 18 hours. The cells were exposed to various concentrations (0.01–30 μM) of compounds for 15 minutes and then to EGF (100 ng/ml) for 10 minutes at 37° C. The cells were scraped and lysates were prepared in the same buffer as described for 32D-αR cells prior to fractionation by conventional SDS PAGE followed by Western blot analysis. For this, proteins were transferred onto nitrocellulose and the membrane was blocked in Tris buffer saline (TBS), pH 7.0, 0.1% Tween 20, 5% dry milk. The membrane was blotted with anti-phosphotyrosine antibody (UBI, 1 μg/ml) in binding buffer (TBS, 0.1% Tween 20; 1% dry milk) for 2 hours at room temperature. Detection was performed using a goat anti-rabbit-horseradish peroxidase conjugated IgG (Boehringer Mannheim). The blot was developed using a chemiluminescent system (Amersham).

In order to measure FGFR-1 autophosphorylation, the human FGFR-1 cDNA was stably over-expressed in CHO cells using standard techniques. These cells were grown to confluency in RPMI with 10% fetal bovine serum, the media was replaced with serum-free RPMI and incubation continued for 18 hours prior to stimulation with βFGF (75 ng/ml) for 10 min. at 37° C. in the absence or presence of PTK inhibitors in a concentration range of 0.1–30 μM. Cell lysates were prepared under the same conditions as described above for the EGFR assay. Lysates were incubated with a monoclonal antibody directed against the FGFR-1 extracellular domain (MAb 1H9D3 which was prepared at COR) and the immunoprecipitated receptor was subjected to SDS-PAGE and Western blot analysis with 4G10 horse radish peroxidase conjugated antiphosphotyrosine antibodies (UBI) and detection was done by chemiluminescence (Amersham).

Figure 1:
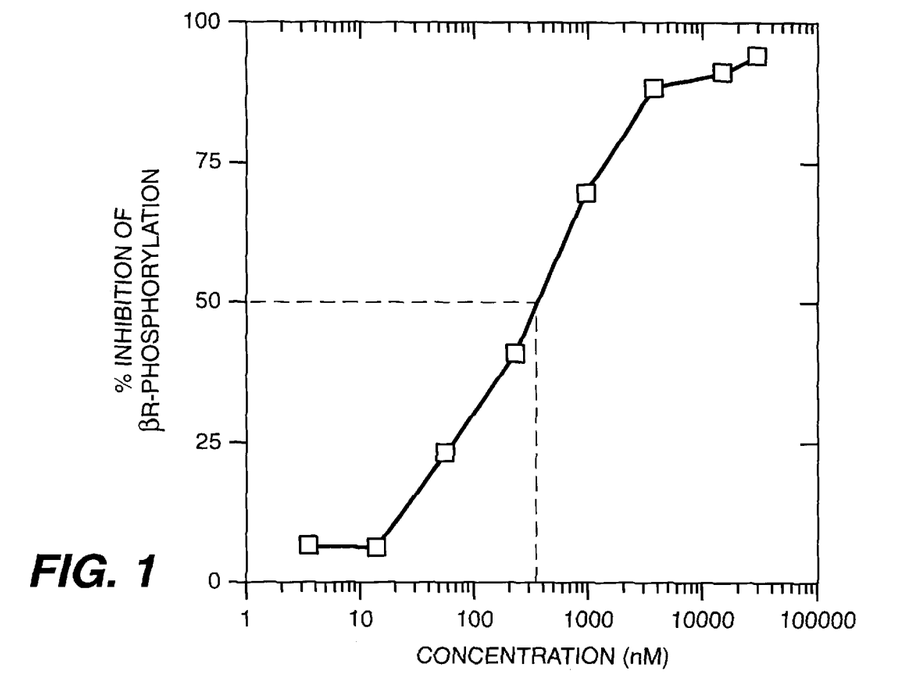
FIG. 1 shows the effect of compound 1 on inhibition of phosphorylation in HR5-βR cells.

As shown in FIG. 1, compound 1 (see Table 1A for structure) efficiently blocked beta PDGFR autophosphorylation in HR5-βR cells with an $IC_{50}$=220 nM and inhibition was maximal at 5 μM. When compared to other potent PTK inhibitors under these conditions, compound 1 was found to be equally potent to K252a and somewhat less potent (three fold) than Staurosporin (see Table 2 below). Also, compound 1 was found to inhibit alpha PDGFR autophosphorylation over the same concentration range as that observed for the beta receptor. These results demonstrate that compound 1 is a potent inhibitor of PDGFR autophosphorylation in intact cells which indicates that this compound will be active in vivo and that therapeutic concentrations should be achievable.

To determine if compound 1 selectively inhibits the PDGFR tyrosine kinase, its effect on the closely related EGFR and FGFR-1 tyrosine kinases were evaluated. Surprisingly, no detectable inhibition of either of these receptors autophosphorylation was observed at concentrations of compound 1 as high as 30 μM. EGFR autophosphorylation was inhibited by K252a ($IC_{50}$=1 μM) but not by Staurosporin at concentrations up to 30 μM (Table 2).

The src PTK family is structurally related to the receptor PTKs as demonstrated by the 60–80% amino acid sequence identity in their enzymatic tyrosine kinase domains. Also, these kinases are functionally similar in that they both mediate intracellular signaling which can result in cellular proliferation. Unlike the receptor PTKs, the src proteins do not contain extracellular or transmembrane domains and therefore do not function directly as receptors for extracellular stimuli. To further test the specificity of compound 1, its ability to inhibit the activity of recombinant c-src (UBI catalog #14-117) was evaluated. In order to adapt this assay to a 96-well microtiter plate format, 0.5 μg of src-substrate peptide-2 (UBI catalog #12-140) was added to each well in 23 mM Tris at pH 8.0, 68 mM NaCl, 14 mM ammonium bicarbonate and 0.01% sodium azide. After peptide immobilization, the wells were washed and then blocked with 25 mM HEPES pH 7.6, 100 mM NaCl, 0.2% Tween 20. The kinase reaction was initiated by adding to each well 100 ml of reaction mixture of which contained test compounds at 0.03–30 μM, 50 μM ATP and 10 units of c-src in 50 mM Tris; pH7, 25 mM $MnCl_2$; 5 mM $MnCl_2$; 0.05 mM $Na_3VO_4$; 100 mM HEPES pH 7; 5% Glycerol and 0.05% nonylphenoxy polyethoxy ethanol (NP-40). After 20 minutes incubation at 37° C., the reactions were stopped by adding 10 μl of 50% acetic acid, the wells were washed and antiphosphotyrosine antibody was used to detect the tyrosine phosphorylated substrate under the same conditions as described above for the detection of phosphorylated PDGFR. As shown in Table 2, compound 1 inhibited src kinase with an $IC_{50}=8.0$ μM which was ~40-fold higher concentration than that required to inhibit PDGFR autophosphorylation. On the other hand, Staurosporin and K252a blocked src kinase activity with $IC_{50}$ values of 70 nM and 20 nM, respectively. These results demonstrate that, whereas compound 1 is selective for inhibiting PDGFR kinase activity, Staurosporin and K252a are equally or more potent at inhibiting src kinase activity as they are PDGFR kinase activity.

Staurosporin is known to be a potent inhibitor of receptor tyrosine kinases, src family tyrosine kinases and the more distantly related serine/threonine kinases. This lack of specificity associated with Staurosporin and other known PTK inhibitors greatly limits their potential as therapeutic agents. To investigate the possibility that compound 1 may inhibit serine/threonine protein kinases, Protein Kinase A (PKA) and Protein Kinase C (PKC) assays were performed using UBI's non-radioactive protein kinase assay under the conditions described by the manufacturer (UBI catalog #17-112). Compound 1 was compared to Staurosporin and K252a by testing each of these compounds over a concentration range of 0.025–40 μM. As shown in Table 2, compound 1 did not achieve a 50% reduction in either PKC or PKA activity at a concentration of 40 μM which is ~200-fold higher than the concentration required to inhibit PDGFR kinase activity. K252a was found to be a potent inhibitor of these serine/threonine kinases with an $IC_{50}$ of 70 nM for PKA and 100 nM for PKC while Staurosporin inhibited both kinases with an $IC_{50}=70$–80 nM. These results demonstrate that while some kinase inhibitors such as Staurosporin and K252a lack selectivity, compound 1 is from 40–200 fold more selective for PDGF receptor than for other receptor tyrosine kinases, src kinases and serine/threonine kinases. Such selectivity greatly enhances the therapeutic potential of compound 1 for the treatment of diseases in which PDGF plays a role such as atherosclerosis, certain cancers, glomerulonephritis and restenosis following angioplasty.

EXAMPLE 2

Inhibition of Cell Proliferation by Pyrazole Compounds

Figure 2:
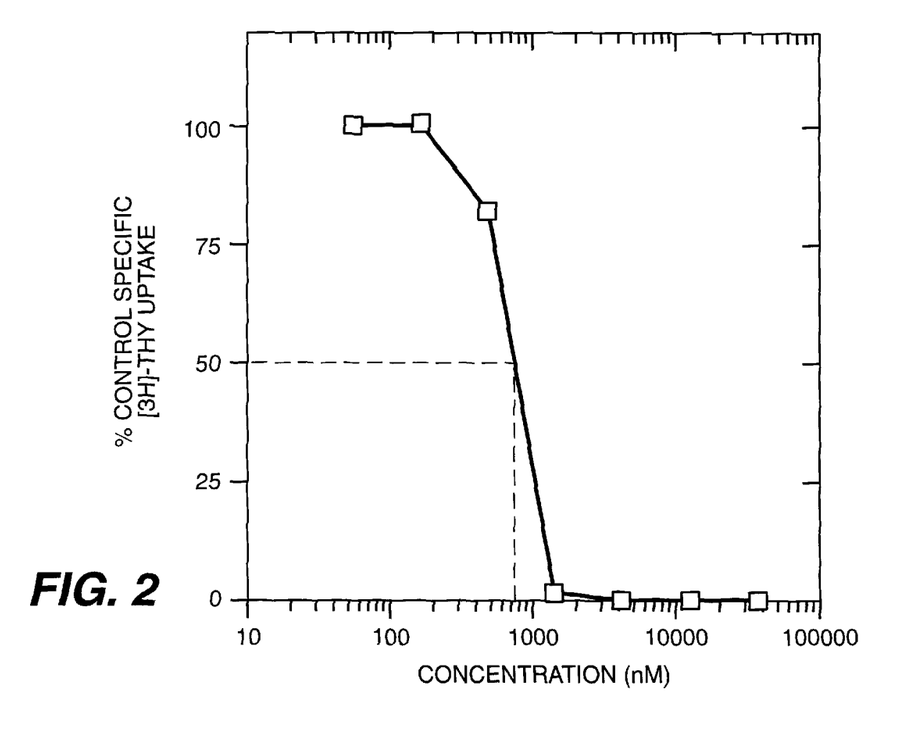
FIG. 2 shows the effect of compound 1 on mitogenic activity in 32D-αR cells.

To determine the potential therapeutic utility of a PTK inhibitor it is important to demonstrate the inhibitor's ability to block cellular proliferation in response to a growth factor that is involved in mediating a proliferative disorder. Since there are many reports in the literature implicating PDGF in diseases such as glomerulonephritis, cancer, atherosclerosis, and restenosis we tested compound 1 for its ability to block PDGF induced cell proliferation. For this purpose 32D-αR cells were used and standard techniques which had been previously developed to measure PDGF induced proliferation were followed. Briefly, 32D-αR cells were grown in interleukin 3 (IL-3)-conditioned RPMI media with 10% fetal bovine serum and washed 2 times with RPMI with 10% fetal bovine serum, resuspended at $5 \times 10^5$ cells/ml in the same media and then dispensed at 250 μl/well in 24 well plates (Falcon). PDGF AA is added at 30 ng/ml in the absence or presence of compound 1 (0.04–40 μM) at a final incubation volume of 0.5 ml. The cells were incubated for 43 hours followed for a further 3 hour incubation with [$^3$H]thymidine (10 μCi/well). The cells are then harvested with an automated cell harvester, filters are placed in liquid scintillation mixture and counted in a β counter. As shown in FIG. 2, compound 1 blocked PDGF induced thymidine incorporation by 50% at 700 nM and completely inhibited mitogenicity at concentrations >1 μM.

To determine if compound 1 exerts a nonspecific antiproliferative effect or is cytotoxic, its effects on the proliferation of human cell lines (e.g. HS68, HS 27, CCD18, and WS1 obtained from ATCC) was determined under standard tissue culture conditions. Cells were sparsely seeded in standard tissue culture medium containing 10% fetal bovine serum at $3.5 \times 10^3$ cells/well in a 96-well microtiter plate (Falcon) in the absence or presence of compound 1, Staurosporin or K252a in the concentration range of 0.01–30 μM. The cells were then allowed to grow under standard tissue culture conditions for 96 hours, at which time they were fixed with 3.3% glutaraldehyde, washed with $H_2O$ and stained with 0.05% methylene blue (Sigma). Following staining, the cells were washed, the dye was eluted with 3% HCl and absorbance was monitored at 665 nM using a plate reader (Molecular Devices). The percentage of inhibition of cell proliferation was determined by comparing the absorbance observed in the presence of inhibitor with the absorbance obtained in the absence of inhibitor. As shown in Table 3, no decrease in cell growth of any of the human cell lines tested was observed following treatment with compound 1 at concentrations up to 10 μM and only a slight decrease (10–20%) occurred at 30 μM. In contrast, Staurosporin completely blocked the growth of all of the human cell lines at 0.01 μM and K252a inhibited cell growth by 50% in the concentration range of 1–12 μM with CCD 18 cells being the most sensitive ($IC_{50}=1$ μM). The effect of these compounds on normal cell growth was also evaluated with HR5-βR cells which were previously used to measure beta PDGFR autophosphorylation. A high concentration (28 μM) of compound 1 was required to inhibit HR5-βr cell growth by 50%. In contrast, Staurosporin ($IC_{50}$<10 nM) and K252a ($IC_{50}$130 nM) potently inhibited HR5-βR cell growth at lower concentrations than those required to inhibit PDGFR phosphorylation. These results demonstrate that Staurosporin, which is a nonspecific protein kinase inhibitor, also exerts a nonspecific antiproliferative or cytotoxic effect at concentrations lower than that required to inhibit kinase activity. On

TABLE 2

| Compound | Inhibition of Protein Kinase Activity $IC_{50}$ [μM] | | | | | | |
| --- | --- | --- | --- | --- | --- | --- | --- |
|  | αPDGFR | βPDGFR | EGFR | FGFR-1 | src-kinase | PKA | PKC |
| cmpd. 1 | .17 | 0.22 | >30 | >30 | 8.0 | >40 | >40 |
| K252a | ND | 0.27 | 1.0 | ND | 0.02 | 0.07 | 0.10 |
| Staurosporin | ND | 0.07 | >30 | ND | 0.07 | 0.07 | 0.08 |

ND = Not Determined the other hand, the concentrations of compound 1 required to inhibit cell growth under standard tissue culture conditions were >100-fold higher than those required to block PDGFR autophosphorylation. These results indicate that the therapeutic effect from inhibiting of PDGFR kinase activity should occur at compound 1 concentrations far below those that cause cytotoxic effects.

TABLE 3

Inhibition of Cell Proliferation Under Normal Tissue Culture Conditions
$IC_{50}$ [μM]

| Compound | Cell Lines | | | | |
|---|---|---|---|---|---|
|  | CCD18 | HS27 | WS1 | HS68 | HRS-βR |
| compound 1 | >30 | >30 | >30 | >30 | 28 |
| Staurosporin | <0.01 | <0.01 | <0.01 | <0.01 | <0.01 |
| K252a | 1.0 | 12 | 5.0 | 5.0 | .13 |

EXAMPLE 3

General: NMR spectra were recorded on a Varian Unity Plus 400 MHz instrument. IR spectra were recorded on a Perkin Elmer Model 1600 FT-IR. Reverse Phase HPLC was performed on a Waters Model 600 Controller with Model 965 PhotoDiodeArray detector using Millenium 2020 software to process the data and either a Vydac 4.5 mm×25 cm C18 analytical column or a Vydac 2.5 cm×25 cm C18 preparative column. Normal Phase HPLC was performed on a Waters DeltaPrep Model 4000 controller with Model 965 PhotoDiodeArray detector using Millenium 2020 software to process the data and either an Alltech Econosil 4.5 mm×25 cm Silica Gel analytical column or an Alltech Econosil 22 mm×25 cm Silica Gel semipreparative column. Flash Column chromatography was performed using E Merck Silica Gel GF. Mass Spectra were performed using either Electron Impact or Direct Chemical Ionization sample introduction techniques.

(A) Preparation of 3-Benzoylamino-5-phenyl-2-benzoylpyrazole (Compound 35)

To a solution of 0.31 g (2.0 mmoles) of 5-amino-3-phenylpyrazole (supplied by Maybridge or Aldrich) dissolved in 5.0 ml pyridine stirring in an ice-water bath under Argon atmosphere was introduced 1.4 ml (12.1 mmoles) of benzoyl chloride. The solution was stirred in the cold bath for 1 hour, warmed to room temperature and stirred for an additional 3½ hours. During reaction, pyridinium hydrochloride separated from solution.

The reaction was quenched by introduction of 10 ml of 10% (v/v) aqueous hydrochloric acid, transferred to a separatory funnel, and extracted twice with 25 ml of dichloromethane. The combined organic extracts were washed with a 10 ml portion of 10% hydrochloric acid, once with saturated sodium chloride solution, dried over magnesium sulfate, and concentrated in vacuo. A white solid was obtained.

The solid was chromatographed on a silica gel semipreparative column using the Waters DeltaPrep instrument. The elution gradient ran from 9:1::hexane:dichloromethane to 1:1::hexane:dichlormethane over 80 minutes at a flow rate of 10 ml per minute. There was obtained 0.37 g (1.0 mrnmoles, 50%) of the title compound as a white solid.

TLC (dichloromethane): $R_f$=0.86; IR (nujol): NH at 3317 cm$^{-1}$, CO at 1689 cm$^{-1}$; NMR (CDCl$_3$): 11.67 (s, NH); 8.21/8.23 (dd, 2 ArH); 8.00/8.02 (dd, 2 ArH); 7.88/7.90 (dd, 2 ArH); 7.58–7.66 (m, 2 ArH); 7.51–7.56 (m, 5 ArH); 7.38–7.48 (m, 3 ArH); MS (EI): M$^+$=367

(B) Preparation of 3-Benzoylamino-5-phenylpyrazole (Compound 1)

A suspension of 100 mg (0.27 mmoles) of 5-benzoylamino-3-phenyl-1-benzoylpyrazole in 4 ml of 10% (w/v) aqueous potassium hydroxide was heated in a water bath maintained at 100° C. for five minutes. During this time the reaction mixture remained a suspension. The cooled suspension was filtered and washed with water, then air-dried. There was obtained 48 mg (0.18 mmoles, 67%) of the title compound as a white solid.

TLC (dichloromethane): $R_f$=0.20; IR (nujol): NH at 3288 cm$^{-1}$, CO at 1656 cm$^{-1}$; NMR (DMSO-d$_6$): 10.80 (s, NH); 7.97/7.99 (dd, 2 ArH); 7.71/7.73 (d, 2 ArH); 7.40–7.56 (m, 5 ArH); 7.29–7.33 (t, ArH); 7.01 (bs, pyrazole CH) MS (EI): M$^+$=263

(C) Preparation of 3-Benzylamino-5-phenylpyrazole (Compound 53)

To a dry 3-necked round bottom flask equipped with a rubber septum, a glass stopper and a reflux condenser with Argon inlet was transferred 0.17 g (0.66 mmoles) of 5-benzoylamino-3-phenylpyrazole. Anhydrous tetrahydrofuran (5 ml) was added via syringe, and stirring at room temperature produced a clear, colorless solution. Introduced to this solution was 0.93 ml (1.86 mmoles) of a commercially available (Aldrich) 2 Molar solution of Borane-Dimethylsulfide Complex in tetrahydrofuran. The solution was refluxed in an oil bath for 17 hours. The reaction solution was cooled to ambient temperature and quenched with 2 ml of 10% (v/v) aqueous hydrochloric acid.

The crude mixture was chromatographed on a C$_{18}$ column using the Waters Model 600 instrument. The elution gradient ran from 100% water (with 0. 1% trifluoroacetic acid "TFA") to 1:1::water:acetonitrile (with 0.1% TFA) over 50 minutes after a 10 minute isocratic wash at 100% water (with 0.1% TFA) at a flow rate of 10 ml per minute. Eluted fractions were analyzed on a C$_{18}$ analytical column using a gradient from 95:5::water:acetonitrile (with 0.1% TFA) to 20:80::water:acetonitrile (with 0.1% TFA) over 30 minutes at a flow rate of 1.5 ml per minute. Appropriate fractions (i.e., those eluting between 38%–44% acetonitrile) were pooled and lyophilized to produce 72.3 mg (0.29 mmoles, 44%) of the title compound as a white powder.

HPLC(C$_{18}$ column): $R_t$=16.9 minutes; NMR (CD$_3$OD): 7.65–7.68 (m, 2 ArH); 7.44–7.47 (m, 3 ArH); 7.31–7.38 (m, 4 ArH); 7.23–7.27 (m, ArH); 4.42 (s, NCH$_2$); MS (EI): M$^+$=249

All publications and patent applications cited herein are incorporated by reference to the same extent as if each individual publication or application was specifically and individually indicated to be incorporated by reference.

It should be understood that the invention is not limited to the particular embodiments shown and described herein, but that various changes and modifications may be made without departing from the spirit and scope of this novel concept as defined by the following claims.

We claim:

1. A method for treating a disease state in mammals that is alleviated by treatment with a protein kinase inhibitor, which method comprises administering to a mammal in need of such a treatment a therapeutically effective amount of a compound of the formula:

wherein:
R$_1$ is, lower hydrocarbyl, aryl lower alkyl, heteroaryl lower alkyl, 5- or 6-membered heterocyclic aromatic, polyaromatic or polyheteroaromatic;

R$_2$ is, lower hydrocarbyl, aryl lower alkyl, heteroaryl lower alkyl, 5- or 6-membered heterocyclic aromatic, lower hydrocarboyl, 5- or 6-membered heterocyclic aromatic carbonyl, polyaromatic, polyaromatic carbonyl, polyheteroaromatic or polyheteroaromatic carbonyl;

R$_3$ is H or lower alkyl;

R$_5$ is H, lower hydrocarbyl, aryl lower alkyl, heteroaryl lower alkyl, 5- or 6-membered heterocyclic aromatic, halogen, or cyano; and R$_6$ is H or lower hydrocarboyl;

wherein each of said, hydrocarbyl, alkylaryl, alkylheteroaryl, hydrocarboyl, or heterocyclic aromatic groups is optionally independently substituted with up to four R$_4$ groups, where each R$_4$ independently represents halogen, cyano, nitro, lower alkyl, hydroxyl, alkoxyl, carbonyl, carboxyl, amino, alkylamino, dialkylamino, or hydrocarboylamido;

or a pharmaceutically acceptable salt thereof:
wherein said compound has an IC$_{10}$ value of about 10 nM–1 $\mu$M.

2. The method of claim 1 wherein R$_1$ is a lower hydrocarbyl or a 5- or 6-membered heterocyclic aromatic, and is optionally substituted with up to four R$_4$ groups.

3. The method of claim 2 wherein said lower hydrocarbyl is a carbocyclic aromatic and is optionally substituted with up to four R$_4$ groups.

4. The method of claim 3 wherein said carbocyclic aromatic is phenyl or phenyl substituted with up to four R$_4$ groups.

5. The method of claim 1 wherein R$_2$ is a lower hydrocarboyl or a 5- or 6-membered heterocyclic aromatic carbonyl, and is optionally substituted with up to four R$_4$ groups.

6. The method of claim 5 wherein said lower hydrocarboyl is a carbocyclic aromatic carbonyl and is optionally substituted with up to four R$_4$ groups.

7. The method of claim 6 wherein said carbocyclic aromatic carbonyl is phenylcarbonyl or phenylcarbonyl substituted with up to four R$_4$ groups.

8. The method of claim 1 wherein R$_3$ is H.

9. The method of claim 1 wherein R$_5$ is H, lower alkyl, halogen or cyano.

10. The method of claim 9 wherein R$_5$ is H.

11. The method of claim 1 wherein R$_6$ is H.

12. The method of claim 1 wherein R$_1$ is, lower hydrocarbyl, or 5- or 6-membered heterocyclic aromatic; R$_2$ is, lower hydrocarbyl, 5- or 6-membered heterocyclic aromatic, lower hydrocarboyl, or 5- or 6-membered hetero-cyclic aromatic carbonyl; R$_3$ is H or lower alkyl; R$_5$ is H, lower alkyl, halogen, or cyano; and R$_6$ is H or lower hydrocarboyl.

13. The method of claim 12, wherein R$_1$ is phenyl or a substituted phenyl, R$_2$ is phenylcarbonyl or substituted phenylcarbonyl, and R$_3$, R$_5$ and R$_6$ are H.

14. The method of claim 13 wherein R$_1$ is phenyl, R$_2$ is benzoyl, and R$_3$, R$_5$ and R$_6$ are H.

15. The method of claim 1, wherein R$_2$ is a phenylcarbonyl or a phenylcarbonyl substituted with an electron-donating or electron neutral substituent relative to H on the phenyl group.

16. The method of claim 1, wherein the disease state is characterized by uncontrolled cell proliferation.

17. The method of claim 16, wherein said disease state is restenosis.

18. A pharmaceutical composition for treating a disease state in mammals characterized by uncontrolled cell proliferation which comprises a kinase inhibiting amount of a compound of the formula:

wherein:
R$_1$ is lower hydrocarbyl, aryl lower alkyl, heteroaryl lower alkyl, 5- or 6-membered heterocyclic aromatic, polyaromatic or polyheteroaromatic;

R$_2$ is lower hydrocarbyl, aryl lower alkyl, heteroaryl lower alkyl, 5- or 6-membered heterocyclic aromatic, lower hydrocarboyl, 5- or 6-membered heterocyclic aromatic carbonyl, polyaromatic, polyaromatic carbonyl, polyheteroaromatic or polyheteroaromatic carbonyl;

R$_3$ is H or lower alkyl;

R$_5$ is H, lower hydrocarbyl, aryl lower alkyl, heteroaryl lower alkyl, 5- or 6-membered heterocyclic aromatic, halogen, or cyano; and R$_6$ is H or lower hydrocarboyl;

wherein each of said hydrocarbyl, alkylaryl, alkylheteroaryl, hydrocarboyl, or heterocyclic aromatic groups is optionally independently substituted with up to four R$_4$ groups, where each R$_4$ independently represents halogen, cyano, nitro, lower alkyl, hydroxyl, alkoxyl, carbonyl, carboxyl, amino, alkylamino, dialkylamino, or hydrocarboylamido; or a pharmaceutically acceptable salt thereof;

wherein said compound has an IC$_{50}$ value of about 10 nM–1 $\mu$M;

in a pharmaceutically acceptable carrier;

with the proviso that when R$_1$ is phenyl or phenyl substituted with lower alkyl, lower alkoxy or halogen; R$_3$ and R$_6$ are H; and R$_5$ is lower alkyl, aryl or aryl substituted with lower alkyl, lower alkoxy or halogen, then R$_2$ can not be lower alkyl.

19. The pharmaceutical composition of claim 18, wherein said disease state is restenosis.

* * * * *